United States Patent

Pelchy et al.

[11] Patent Number: 5,857,963
[45] Date of Patent: Jan. 12, 1999

[54] TAB IMAGER ASSEMBLY FOR USE IN AN ENDOSCOPE

[75] Inventors: Thomas Edward Pelchy, Moravia; James Edward Grecco, Camillus; Edward Arthur Johnson, Skaneateles; Robert L. Vivenzio, Auburn; Douglas J. West, Skaneateles; Richard L. Bingham, Preble, all of N.Y.

[73] Assignee: Welch Allyn, Inc., Skaneateles Falls, N.Y.

[21] Appl. No.: 682,136

[22] Filed: Jul. 17, 1996

[51] Int. Cl.$^6$ .......................................................... A61B 1/05
[52] U.S. Cl. ............................................. 600/109; 348/373
[58] Field of Search .................................... 600/109–112; 348/65, 76, 373, 375, 294; 250/239

[56] References Cited

U.S. PATENT DOCUMENTS

| | | |
|---|---|---|
| 4,491,865 | 1/1985 | Danna et al. . |
| 4,706,654 | 11/1987 | Ogiu et al. . |
| 4,745,470 | 5/1988 | Yabe et al. ............................... 600/109 |
| 4,745,471 | 5/1988 | Takamura et al. . |
| 4,757,805 | 7/1988 | Yabe . |
| 4,777,524 | 10/1988 | Nakajima et al. ....................... 600/109 |
| 4,779,130 | 10/1988 | Yabe ....................................... 600/109 |
| 4,786,965 | 11/1988 | Yabe . |
| 4,918,521 | 4/1990 | Yabe et al. . |
| 4,993,405 | 2/1991 | Takamura et al. ......................... 348/65 |
| 5,051,824 | 9/1991 | Yabe et al. . |
| 5,220,198 | 6/1993 | Tsuji ......................................... 348/75 |
| 5,305,736 | 4/1994 | Ito ............................................ 600/109 |

Primary Examiner—John P. Leubecker
Attorney, Agent, or Firm—Wall Marjama Bilinski & Burr

[57] ABSTRACT

A solid state imager assembly for use in an endoscope in which a TAB imager package is mounted within the horizontal leg of a T-shaped support member. Circuitry for servicing the imager is mounted on the vertical leg of the support member. In one embodiment of the invention, the vertical component of the T-shaped support member comprises two half-sections.

22 Claims, 4 Drawing Sheets

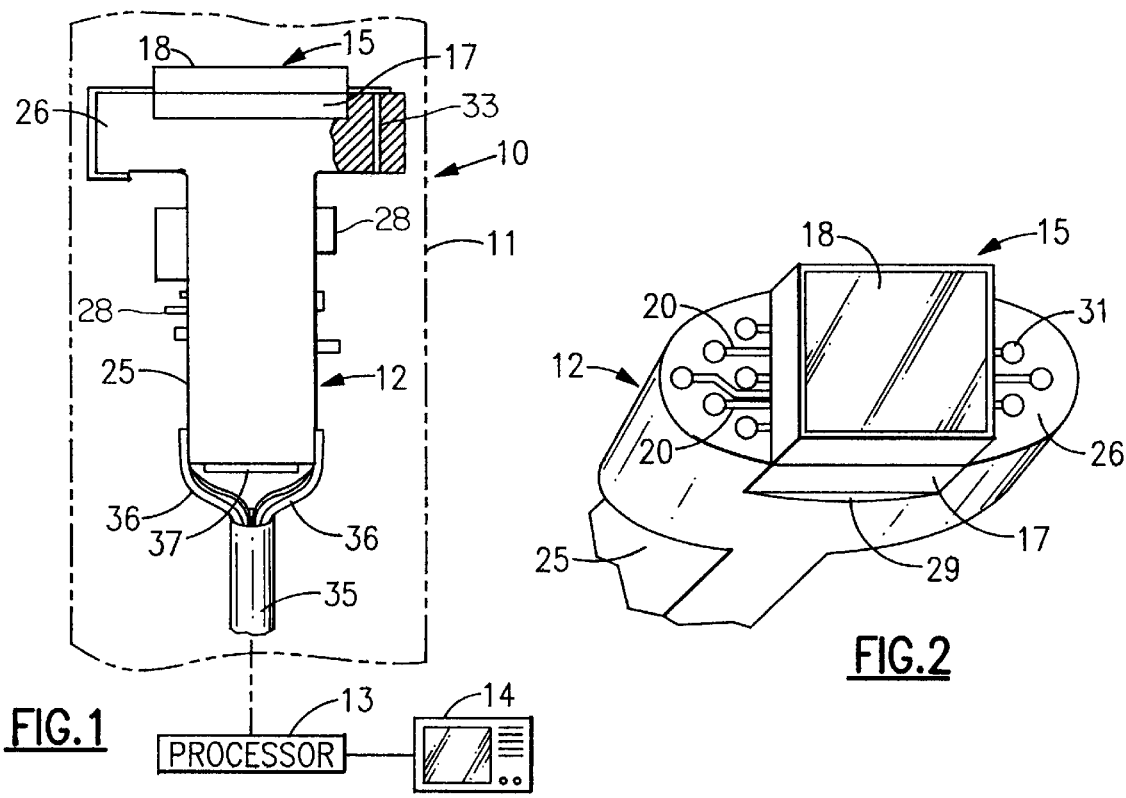
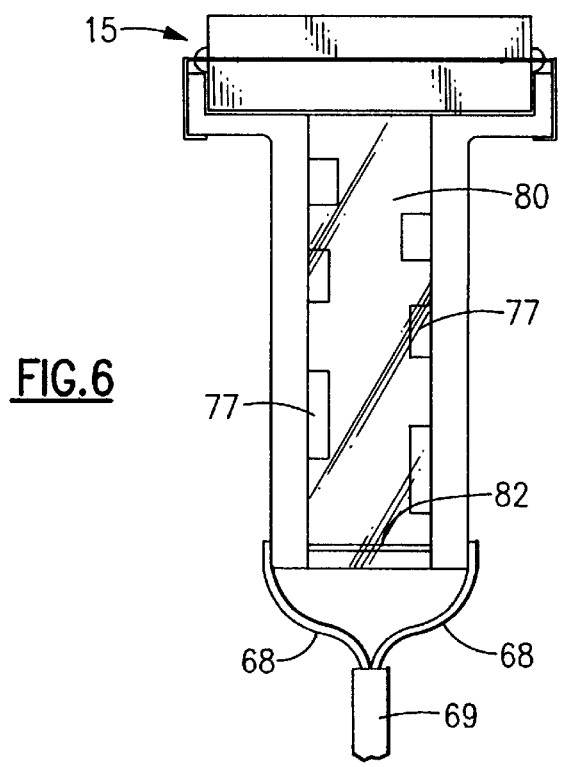
FIG. 1
FIG. 2
FIG. 6

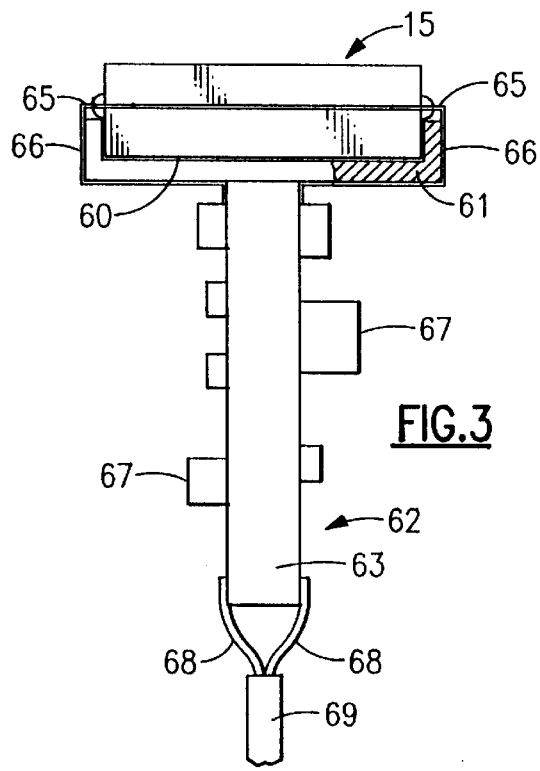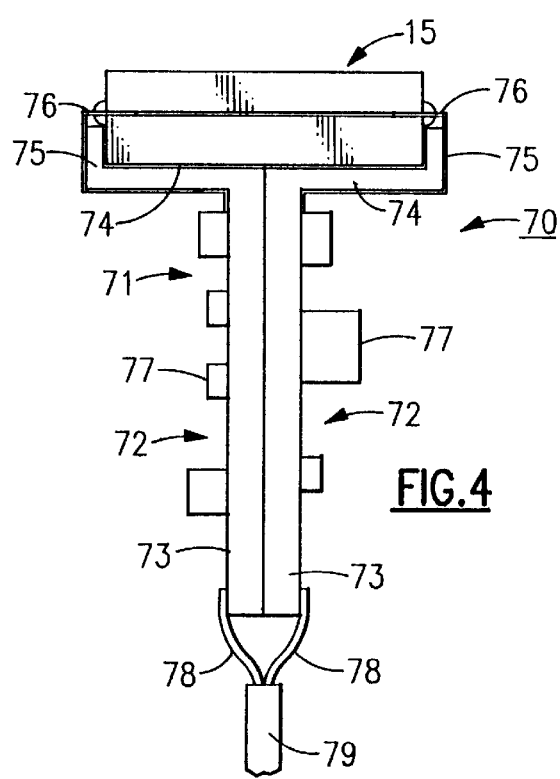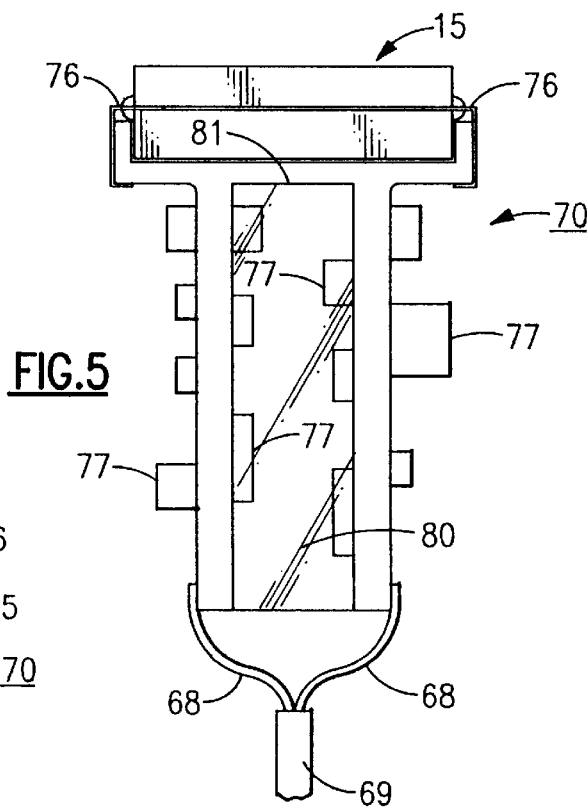

TAB IMAGER ASSEMBLY FOR USE IN AN ENDOSCOPE

BACKGROUND OF THE INVENTION

This invention relates to a solid state imager assembly and, in particular, to a highly compact imager assembly suitable for use in a video endoscope.

The increased availability of smaller solid state imagers based on CCD or CMOS technologies has surpassed the ability of conventional wire bonding techniques to take full advantage of the space savings afforded by these small imagers. An advanced integrated circuit technology known as the tape automated bonding (TAB) process has been developed which permits fine line high pitch lead patterns to be bonded to extremely small electronic components such as CCD imagers. In this process the imager is supported on a thin flexible substrate and the high density imager leads are TAB die bonded to the substrate. The high pitch leads typically extend outwardly from both sides of the imager for a distance sufficient to allow the leads to be connected to other electrical components using more conventional bonding techniques. A transparent window, typically being glass, is placed over the imager and the extended leads to complete the package. This package will be herein referred to as a TAB imager or TAB imager package.

TAB packages are structurally relatively weak and are normally mounted on a flat support such as an IC board, along with other electrical components. The TAB boards, however, are rather bulky and space consuming and thus do not lend themselves for use in confined regions such as in the camera head of a video endoscope.

SUMMARY OF THE INVENTION

It is therefore an object of the present invention to improve the packaging of solid state imagers It is a further object of the present invention to improve the packaging of a solid state imager unit employing the TAB bonding process.

A still further object of the present invention is to further compact imager and circuitry assemblies used in the insertion tube of a video endoscope.

Another object of the present invention is to decrease the size of an insertion tube used in a video endoscope.

Yet another object of the present invention is to provide a compact camera head for a video endoscope that is both rugged and insensitive to changes in ambient conditions.

These and other objects of the present invention are attained by a solid state imager assembly that includes a T-shaped nonconductive support member having a vertical member and a horizontal member. The horizontal member contains a recess that passes downwardly through the top surface thereof to a given depth. A TAB imager package that includes a solid state imager, a transparent window mounted over the imager and fine pitched lead extending outwardly from between the imager and the window to both sides of the imager. Circuitry is mounted upon the vertical member of the support and is connected to the leads by traces contained on or in the support member.

In one form of the invention, the support member is separated along a vertical axis into the symmetrical half sections to facilitate manufacture and assembly of the components.

BRIEF DESCRIPTION OF THE DRAWINGS

For a better understanding of these and other objects of the present invention, reference will be made to the following detailed description of the invention which is to be read in association with the following drawings, wherein:

FIG. 1 is a side elevation showing an imager assembly embodying the present invention;

FIG. 2 is a partial perspective view showing the assembly in FIG. 1;

FIG. 3 is a side elevation illustrating a further embodiment of the invention;

FIG. 4 is another side elevation showing a still further embodiment of the invention;

FIG. 5 is a side elevation showing another embodiment of the invention;

FIG. 6 is also a side elevation showing yet another object of the invention;

DESCRIPTION OF THE INVENTION

Figure 8:
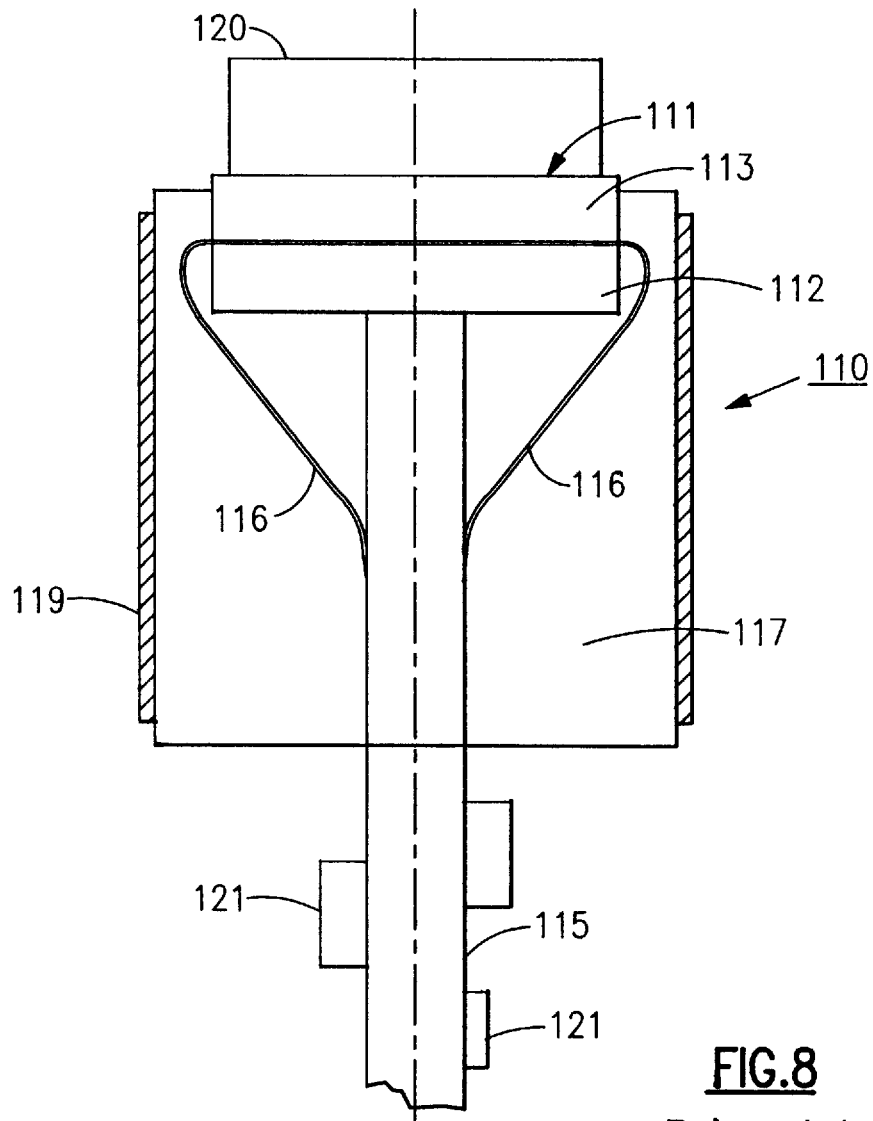
FIG. 8 is an enlarged side elevation showing a prior art imager package.

Turning initially to FIG. 8, there is shown a prior art TAB imager assembly generally referenced 110. The assembly includes a TAB imager package 111 that includes a solid state imager 112 which is protectively covered with a transparent window 113. The imager package is centrally mounted upon the top edge of an elongated circuit board 115. The imager leads 116, which extend outwardly from between the window and the imager to both sides of the imager are turned downwardly and are bonded to either side of the circuit board. A block 117 of epoxy resin is placed about the imager package and the circuit board to bond the two together in assembly. The block of resin is enclosed in a metal band 119 and a second glass window 120 is placed over the imager. Circuit means 121-121 are contained on either side of the circuit board and is connected to the leads by suitable electrical traces.

Although the prior art TAB imager package is somewhat compacted in width when compared to similar packages, it nevertheless is relatively greater in length. Because of the extended length, the prior art package does not lend itself for use in a video endoscope wherein the distal end of the insertion tube must be articulated to maneuver the tube around sharp corners or bends.

Referring now to FIGS. 1 and 2, there is shown a video endoscopic system, generally referenced 10, embodying the teachings of the present invention. The system includes an elongated insertion tube 11 containing a small solid state imager assembly 12 mounted at its distal end that is capable of recording an image of a target positioned within the viewing range of the system. The recorded image data is converted to electrical readout signals that are transmitted by wires that pass back through the insertion tube to a video processor 13. In the processor, the image information is placed in a format for either direct viewing by a video monitor 14 or storage for future viewing in a video recorder (not shown).

The insertion tube is provided with a steering capability for articulating the distal end of the tube that houses the imager assembly. The instrument may further include other functional components that are known and used in the art such as lighting for illuminating the target region and air and water delivery systems for carrying out various related procedures.

Since the introduction of the video endoscope in the early 1980's, the trend in the industry has been towards reducing the size of the insertion tube which is generally limited by the size of the imager package. Advances in electronic packaging have made available extremely small CCD imagers and electronic components for servicing the imagers. Small imagers requiring fine pitch lead spacing at or below 2 mm are being manufactured using the tape automated bonding process (TAB) where, as noted above, the imager is mounted upon a thin film support and a transparent window is laced over the imager. The fine pitch leads typically extend outwardly from between the imager and the window to either side of the imager. TAB imager packages have little structural strength and are generally placed on flat circuit boards in along with other related circuitry. As should be evident, this type of flat packaging takes up a good deal of space and thus does not lent itself for use in a confined space such as at the distal end of a video endoscope insertion tube.

As illustrated in FIGS. 1 and 2, the imager assembly of the present invention includes a TAB imager package generally referenced 15 that includes a CCD imager 17 and a glass window 18 mounted thereover to protect the image recording surface of the imager. A series of high pitch leads 20-20 extend outwardly from between the window and the imager to either side of the imager. The pitch between the leads is at or below 2 mm. The TAB imager package is mounted in a T-shaped support member that is formed of a non-conductive material such as ceramic, alumina, or the like. The support member includes a vertical member 25 and a horizontal leg 26. The length of each member is substantially equal to the top to bottom length of the imager. Circuitry 28 is mounted on either side wall of the vertical member for processing input and output signals to the imager. A recess 29 is formed in the top surface of the horizontal leg to a depth that is substantially equal to the thickness of the imager. Accordingly, the imager leads pass directly over the top surface of the horizontal member 26 of the support. Bonding pads 31-31 are mounted on the top surface of the horizontal member and the leads are bonded to the pads. The pads, in turn, are connected to traces 33, not shown, that pass downwardly through the horizontal member and are brought out along the vertical member to the electrical components 28-28 mounted thereon. A grounding buss 37 for the circuitry is mounted upon the bottom surface of the vertical member 25.

A wire bundle 35 runs through the insertion tube which contains transmission wires 36-36 for connecting the electrical circuitry on the support member to the video processor.

Figure 7:
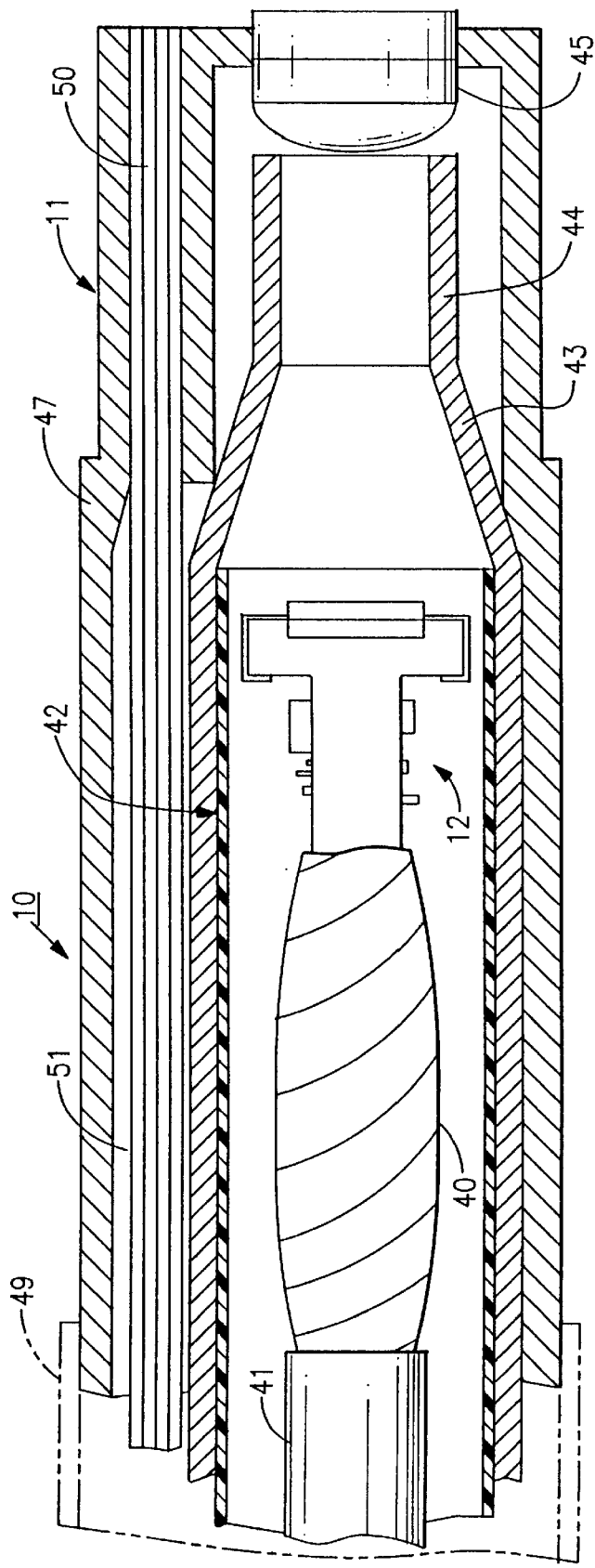
FIG. 7 is an enlarged side elevation showing in greater detail the distal end of an insertion tube of a video endoscope containing the imager assembly of the present invention.

The imager assembly 12 described with reference to FIGS. 1 and 2 is shown in FIG. 7 mounted in the distal end of the insertion tube 11 of a video endoscope 10. The body of the imager support and the wire bundle is wrapped with a heat shrinkable Mylar tape 40 and the wire bundle is passed into a sheath 41. The imager window remains unwrapped and the imager is able to clearly view a target positioned in front of the lens system 45 mounted in the end face of the insertion tube. The wrapped imager package is placed within a thin walled cylinder 42 made of nickel that fits closely about the imager assembly. The cylinder has a necked down section 43 that enters a small front section 44. The front section is positioned adjacent the lens system which may contain one or more lens elements for focussing a target image upon the recording surface of the imager.

A housing 47 is placed over the nickel container as illustrated in FIG. 8 and is secured to the outer casing 49 of the insertion tube. A light carrying fiber bundle 50 is arranged to pass through an axially disposed channel 51 in the housing. The fiber bundle transmits light from a light source in the processor and directs the light into the target region.

FIG. 3 illustrates a second embodiment of the invention wherein the imager assembly once again includes a TAB imager package 15 that is mounted in a recess 60 formed in the horizontal member 61 of a T-shaped support element 62. In this case, the vertical member 63 of the support 62 is a separate piece that is bonded to the horizontal member by any suitable means such as conductive epoxy, solder fillet, or the like. The imager leads 65-65 extend to either side of the TAB imager package and are bonded to electrical traces 66-66 that are attached to associated traces on the vertical leg when the two legs are bonded together in assembly. This, in turn, places the electrical circuitry 67-67 mounted on either side of the vertical leg in communication with the imager. Transmission wires 68-68 are also attached to both sides of the vertical member and are carried back through the insertion tube to the process by the bundle 69.

Turning now to FIG. 4, there is shown an imager assembly 70 that includes a support 71 that is formed of two symmetrical half sections 72-72. The half sections are bonded in a face-to-face relationship in assembly. Each half section includes a vertical panel 73, a horizontal shelf 74 and a raised vertical lip 75 that are integrally formed from a separate piece of conductive material. When the half sections are brought together in assembly, a recess is formed in the top section of the support in which the TAB imager package 15 is seated. Here again, the imager leads 76-76 are bonded to suitable traces printed on or in the half sections to place the imager in communication with circuitry 77-77 mounted on each of the vertical panels. Transmission wires 78-78 are attached to the panel for coupling the circuitry to a video processor via bundle 79.

FIG. 5 is a still further embodiment of the invention which is similar to that shown in FIG. 4 where like numerals depict like components. In this embodiment, the vertical panels 73-73 of the two-piece support 71 are separated in assembly and circuitry 77 is mounted on both sides o the panels. The gap between the panels may be filled with a block encapsulating material 80, such as epoxy resin, which is bonded to both panels as well as the bottom of the imager package 15. As can be seen in this embodiment of the invention, greater surface area is provided for mounting additional circuitry close to the TAB imager package. A connector 81 passes under the imager package and serves to place the circuitry on one half-section in communication with that on the other half section.

FIG. 6, again, illustrates an embodiment of the invention that is similar to that illustrated in FIG. 5. In this embodiment, circuitry 77 is mounted only on the inside surfaces of the vertical panels 73-73. The circuitry, as noted above, is again encapsulated within a block 80 of epoxy resin. A connector 82 is either passed through the resin block or under the imager as shown in FIG. 5, again, to place the circuitry on one-half section in communication with that on the other half section. In this embodiment, all of the circuitry mounted upon the support member is completely protected from moisture or the like.

While this invention has been explained with reference to the structure disclosed herein, it is not confined to the details set forth and this invention is intended to cover any modifications and changes as may come within the scope of the following claims:

What is claimed is:

1. A solid state imager assembly comprising:
   a T-shaped non-conductive support having a vertical member and a horizontal member,
   said horizontal member having a recess passing downwardly through a top surface of said member to a given uniform depth, a TAB imager package mounted in said recess, said package including a solid state imager, a transparent window mounted over said imager and fine pitch leads extending outwardly from between the imager and the transparent window to either side of the package so that the leads overlie at least a portion of the top surface of the horizontal member, the pitch of said leads being about 2 mm or less, said TAB imager package being entirely supported by said non-conductive support, circuit means mounted upon said support for transmitting signals to and from said solid state imager, and traces on said support for electrically connecting said imager leads to said circuit means.

2. The imager assembly of claim 1 wherein the pitch between leads is 2 mm or less.

3. The imager assembly of claim 1 wherein said circuit means is located on at least one side of the vertical member of said support.

4. The imager assembly of claim 1 that further includes a grounding buss for said circuit means mounted upon the bottom surface of the vertical member.

5. The imager assembly of claim 1 wherein said support is formed from a single piece of non-conductive material.

6. The imager assembly of claim 1 wherein the vertical member and the horizontal member of said support are separate sections that are bonded together in assembly.

7. The imager assembly of claim 6 wherein said imager leads pass over the top surface of the horizontal member and are bonded to electrical traces mounted upon the support for connecting the imager to said circuitry.

8. The imager assembly of claim 1 that further includes transmission wires connected to the vertical member of said support for connecting the electrical circuitry on said support member to a remote video processor.

9. A solid state imager assembly comprising:

a non-conductive support including two half-sections that are symmetrically positioned about a common central axis, each half section further including a vertical panel, a horizontal shelf extending outwardly from the top edge of the vertical panel and a raised lip extending vertically from the outer edge of said shelf, a TAB imager package mounted upon the shelves of the two half sections, said package including a solid state imager that is seated upon said shelf adjacent said lips, a transparent window mounted upon the imager and fine pitch leads extending outwardly to either side of the imager over the opposed lips of said support, circuit means mounted upon the vertical panel of each half section for transmitting signals to and from said solid state imager, and electrical traces on each of the half sections for electrically connecting said fine pitch leads to said circuit means.

10. The imager assembly of claim 9 wherein the pitch between leads is at or below 2 mm.

11. The imager assembly of claim 9 wherein the height of the opposed lips above the top of the shelves are about equal to the height of the imager.

12. The imager assembly of claim 9 wherein the opposing side walls of the vertical panels are bonded together in abutting contact in assembly and said circuit means are mounted on the outer side walls of the abutting panels.

13. The imager assembly of claim 9 wherein a gap is provided between the opposing side walls of the panels and circuit means are mounted on both sides of each panel and further including a block of encapsulating material filling said gap which is bonded to each of said panels.

14. The imager assembly of claim 9 wherein a gap is provided between the opposing side walls of the panels, and circuit means are mounted on the inner side walls of the panels, and said imager assembly further including a block of encapsulating material filling said gap, said block being bonded to the opposing panels whereby the electrical circuitry mounted upon the panels is completely encapsulated in said material.

15. The imager assembly of claim 14 that further includes at least one electrical connection for coupling the electric circuitry mounted on one half section with that mounted on the other half section.

16. A video endoscope having an insertion tube and a video processor, said endoscope including:

a light bundle passing through said insertion tube having a light exit face located at a distal end of the insertion tube for illuminating a target, lens means mounted in the distal end of the insertion tube for focussing an image of said target upon an imaging plane located inside said insertion tube, a TAB imager package including a solid state imager, a transparent window mounted over the imager, and fine pitch leads passing from between the window and the imager to either side of the imager, a T-shaped non conductive support having a first member mounted perpendicular to the axis of the insertion tube and a second member integral with said first member being mounted along said axis, said first member having a recess formed in the top surface thereof in which said TAB imager package is seated with said leads passing over the top of said first member, and an image recording surface on the imager lying in said plane, electrical circuitry means mounted upon the second member of said support and electrical traces on said support for connecting said electrical circuitry means to said leads, wherein said T-shaped non conductive support is disposed within a thin walled cylinder of said endoscope contained within said insertion tube, and in which said non conductive support is not in contact with said thin walled cylinder such that said TAB imager assembly is not supported by said thin walled cylinder, and transmission wires connected to the second member of said support that extend through the insertion tube for exchanging signals between said electrical circuitry means and a remote video processor.

17. The video endoscope of claim 16 wherein the pitch between leads is 2 mm or less.

18. The video endoscope of claim 16 that further includes a common ground buss for said circuitry mounted along the bottom edge of said second member.

19. A video endoscope having an insertion tube and a video processor, said endoscope including:

a light bundle passing through said insertion tube having a light exit face located at a distal end of the insertion tube for illuminating a target, lens means mounted in the distal end of the insertion tube for focussing an image of said target upon a plane located inside said insertion tube, a TAB imager package including a solid state imager, a transparent window mounted over said imager and fine pitch leads passing from between the window and the imager to either side of the imager, a T-shaped non conductive support having a first member mounted perpendicularly to the axis of the insertion tube and a second member being mounted along said axis, said first member having a recess formed in the top surface thereof in which said TAB imager package is seated with said pitch leads passing over the top of said first member, and an image recording surface on the imager lying within said plane, wherein said second member is divided into two symmetrical half sections, each of which includes a panel parallely aligned with the axis of the insertion tube, electrical circuitry means mounted upon the second member of said support and electrical traces on said support for connecting said electrical circuitry means to said leads, and transmission wires connected to the second member of said support that extends through the insertion tube for exchanging signals between said electrical circuitry means and a remote video processor.

20. The video endoscope of claim 19 wherein the vertical panels are separated to provide a gap therebetween and said electrical circuitry is mounted on each vertical panel.

21. The video endoscope of claim 19 wherein said electrical circuitry is mounted on the opposing inner sides of said vertical panels and further includes a block of encapsulating material filling the gap between panels, said block being bonded to said panels and encapsulating said electrical circuitry mounted thereon.

22. The video endoscope of claim 21 that further includes connecting means for electrically coupling the circuit means on one panel with circuit means on the other panel.

* * * * *